US006654629B2

(12) United States Patent
Montegrande

(10) Patent No.: US 6,654,629 B2
(45) Date of Patent: Nov. 25, 2003

(54) IMPLANTABLE BIOMARKER AND METHOD OF USE

(76) Inventor: Valentino Montegrande, 1150 Main St., Irvine, CA (US) 92614

( * ) Notice: Subject to any disclaimer, the term of this patent is extended or adjusted under 35 U.S.C. 154(b) by 0 days.

(21) Appl. No.: 10/120,721

(22) Filed: Apr. 11, 2002

(65) Prior Publication Data

US 2003/0139669 A1 Jul. 24, 2003

Related U.S. Application Data

(60) Provisional application No. 60/351,122, filed on Jan. 23, 2002.

(51) Int. Cl.[7] .............. A61B 5/00; A61B 8/00
(52) U.S. Cl. .......... 600/424; 600/439; 600/458
(58) Field of Search .......... 600/407, 410–424, 600/426–427, 439, 458, 461; 604/100, 117, 20, 22; 606/1, 96, 98, 102, 104

(56) References Cited

U.S. PATENT DOCUMENTS

| 3,818,894 A | 6/1974 | Wichterele et al. |
| 4,007,732 A | 2/1977 | Kvavle et al. |
| 4,041,931 A | 8/1977 | Elliot et al. |
| 4,202,349 A | 5/1980 | Jones |
| 4,331,654 A | 5/1982 | Morris |
| 4,693,237 A | 9/1987 | Hoffman et al. |
| 4,909,250 A | 3/1990 | Smith |
| 5,236,410 A | 8/1993 | Granov et al. |
| 5,281,408 A | 1/1994 | Unger |
| 5,282,781 A | 2/1994 | Liprie |
| 5,284,059 A | 2/1994 | Wan |
| 5,334,381 A | 8/1994 | Unger |
| 5,422,730 A | 6/1995 | Barlow et al. |
| 5,494,030 A | 2/1996 | Swartz et al. |
| 5,636,255 A | 6/1997 | Ellis |
| 5,664,582 A | 9/1997 | Szymaitis |
| 5,676,146 A | 10/1997 | Scarborough |
| 5,676,925 A | 10/1997 | Klaveness et al. |
| 5,688,490 A | 11/1997 | Tournier et al. |
| 5,782,765 A | 7/1998 | Jonkman |
| 5,853,366 A | 12/1998 | Dowlatshahi |
| 5,902,310 A | 5/1999 | Foerster et al. |
| 5,941,890 A | 8/1999 | Voegele et al. |
| 5,964,701 A * | 10/1999 | Asada et al. .............. 600/300 |
| 6,026,818 A | 2/2000 | Blair et al. |
| 6,128,961 A * | 10/2000 | Haronian .................. 73/774 |
| 6,161,034 A | 12/2000 | Burbank et al. |
| 6,173,715 B1 | 1/2001 | Sinanan et al. |
| 6,181,960 B1 | 1/2001 | Jensen et al. |
| 6,235,038 B1 | 5/2001 | Hunter et al. |
| 6,246,898 B1 | 6/2001 | Vesely et al. |
| 6,261,247 B1 | 7/2001 | Ishikawa et al. |
| 6,270,464 B1 | 8/2001 | Fulton, III et al. |
| 6,305,381 B1 | 10/2001 | Weijand et al. |
| 6,368,275 B1 * | 4/2002 | Sliwa et al. .............. 600/437 |
| 2002/0013539 A1 * | 1/2002 | Hung ...................... 600/573 |
| 2002/0017834 A1 * | 2/2002 | MacDonald .............. 310/328 |
| 2002/0049394 A1 * | 4/2002 | Roy et al. ................ 600/594 |

FOREIGN PATENT DOCUMENTS

| EP | 0 481 685 A1 | 4/1992 |
| EP | 0 679 372 A2 | 2/1995 |
| WO | WO 9608208 A1 | 3/1996 |
| WO | WO 98/06346 | 2/1998 |

* cited by examiner

Primary Examiner—Francis J. Jaworski
(74) Attorney, Agent, or Firm—Eric Karich

(57) ABSTRACT

The present invention provides an implantable biomarker for finding a location inside a patient while performing minimally invasive or open surgical procedures. The implantable biomarker includes a dielectric base that includes two opposing sides from which extend a plurality of wave-guide rods. The implantable biomarker is preferably mounted upon a surgical instrument or surgical implant and used in conjunction with an image-guided system to enable a surgeon to quickly and easily find the location without requiring extensive x-rays or the use of expensive and cumbersome equipment.

22 Claims, 5 Drawing Sheets

IMPLANTABLE BIOMARKER AND METHOD OF USE

CROSS-REFERENCE TO RELATED APPLICATIONS

This application for a utility patent claims the benefit of U.S. Provisional Application No. 60/351,122, filed Jan. 23, 2002, which is hereby incorporated by reference in its entirety.

STATEMENT REGARDING FEDERALLY SPONSORED RESEARCH

Not Applicable

BACKGROUND OF THE INVENTION

1. Field of the Invention

This invention relates generally to biomarkers, and more particularly to an implantable biomarker that can be used as part of an image guided system that utilizes ultrasound imaging techniques.

2. Description of Related Art

The first class of prior art biomarkers include materials that have different ultrasound reflective properties and only remain in the body temporarily, eventually being reabsorbed by the body. An example of this technology is shown in Burbank et al., U.S. Pat. No. 6,161,034, assigned to SENOREX®, that teaches detectable markers that may be introduced by a cavity created by removal of a biopsy specimen to mark the location of the biopsy site so that it may be located in a subsequent medical/surgical procedure. The marker preferably includes gasses, saline solutions, or similar materials. The markers remain present in sufficient quantity to permit detection and location of the biopsy site at the first time point (e.g., 2 weeks) after introduction but clear from the biopsy site or otherwise not interfere with imaging of tissues adjacent the biopsy site at a second time point several months after introduction.

Unger, U.S. Pat. No. 5,281,408 teaches a substantially homogeneous aqueous suspensions of low density microspheres which are presented as contrast media for imaging the gastrointestinal tract and other body cavities using computed tomography. In one embodiment, the low density microspheres are gas-filled. With computed tomography, the contrast media serve to change the relative density of certain areas within the gastrointestinal tract and other body cavities, and improve the overall diagnostic efficacy of this imaging method.

Unger, U.S. Pat. No. 5,334,381 teaches liposomes suitable as ultrasound contrast agents which contain media of various types including gases, gaseous precursors activated by pH, temperature or pressure, as well as other solid or liquid contrast enhancing agents. Methods of using and synthesizing the ultrasound contrast agents are also disclosed.

Klaveness et al., U.S. Pat. No. 5,676,925, teaches a gas containing, or gas generating, polymer microparticles or microballoons used as a contrast agent in ultrasound imaging.

Scarborough, U.S. Pat. No. 5,676,146 teaches a surgical implant containing a resorbable radiopaque marker that enables the position and/or orientation of the implant to be readily determined by x-ray or other radiographic technique following its surgical implantation into the body. Smith, U.S. Pat. No. 4,909,250 teaches a an animal identification system for swine or other livestock which employs an identification implant or pellet consisting of food grade material and imprinted with information to identify the source of the animal and its carcass after slaughter. The pellet is implanted under the hide or skin of the animal for purposes of identification. In the case of swine, the identification pellet is located in the fat layer of the shoulder area underneath its hide or skin. The pellet and the imprinted information consist of food grade material which is capable of being dissolved with the fat layer or disintegrated into cracklings in a rendering process. The pellet remains in the carcass after the animal is slaughtered until its removal to permit identification of the source of the animal. If the pellet is not removed, it is either dissolved with the fat of the animal or disintegrated into cracklings in the rendering process. Installation tools are disclosed for implanting the identification pellet in a horizontal or vertical orientation under the hide or skin of the animal.

Many references utilize metal reference markers that are then observed using x-rays. Example of these devices are as follows:

Kvavle et al., U.S. Pat. No. 4,007,732 describes X-ray techniques that are used to detect early evidence of breast cancer. When such evidence is found, a target is implanted in the suspect area while the patient is being x-rayed. The target has an attached line which leads from the target out through the skin of the patient. A biopsy is made with a cutting tool guided on the line attached to the target, thereby obtaining a biopsy specimen accurately centered on the suspect area.

Liprie, U.S. Pat. No. 5,282,781 teaches a composite source wire for use in treating malignant tumors within a patient's body by localized in vivo radiation with a radioactive source, via a catheter providing a path from a point external to the body to the tumor site. The source wire includes a thin continuous cylindrical flexible elongate stainless steel tube having encased therein a backbone wire running from its proximal end to a point short of its distal end to strengthen and enhance its flexibility, a cylindrical radioactive core adjacent to the distal end in abutting relation to the backbone wire, and a cylindrical plug at the distal end in abutting relation to the other end of the core, with the backbone wire, core and plug being tightly secured within the tube and the tube being securely enclosed about the plug with a tapered tip portion formed at that point. The source wire has an overall diameter sized to permit ease of movement through the catheter in advancement to the tumor site for the radiation treatment and to allow its retraction through the catheter from the point external to the body. The exterior surface of the tube is gold plated from its tip to the far end of the portion overlying the core. The source wire has an extremely small diameter (under 0.7 mm) and is sufficiently flexible that even in high radioactive dose sizes it is capable of passing through very narrow and even kinked catheters, making it useful for treating inoperable tumors such as common bile duct pancreatic cancer.

Hoffinan et al., U.S. Pat. No. 4,693,237 describes marker members of radiopaque material in the form of bands each of a different geometric configuration which are sutured to the point at which a surgical graft to a blood vessel is made as in a coronary bypass operation. These ring or other shaped radiopaque members provide markers identifying the exact coronary blood vessel that the graft will lead to, each geometrical shape identifying a different coronary vessel bypassed, thus facilitating bypass graft catherization by identifying the entry point of any specific bypass graft.

Lam et al., 0 679 372 A2 teaches a radiopaque marker associated with a stent which is adapted to be implanted into a body lumen of a patient to maintain the patency thereof and a convenient and accurate method for affixing the radiopaque marker to the stent. The radiopaque marker defining an acceptable profile and capable of facilitating, under fluoroscopy, the identification of the position, diameter and length of a stent without obscuring the lesion being repaired and without impeding the deformation of an expendable stent.

Bahler et al., EP 0 146 699 A1 teaches implants consisting of contrast body and anchoring body fixed positionally secure in the bone with the aid of a structure of the anchoring body and thus form, in the bone, immovable reference points for the measurement of x-ray pictures.

Ellis, U.S. Pat. No. 5,636,255, describes a method and system for correlating accuracy of computer tomography (CT) image resolution. Small radio-opaque markers having a diameter less than one slice width of a CT scan are embedded in the object, such as a bony skeletal member, to be measured, the object is then CT scanned so that the radio-opaque markers appear in at two slices of the scan. The markers are also physically located by detecting them with a sensor, such as a positioning pointer. Also described is one form of marker comprising a tantalum to sphere mounted in a ceramic, preferably alumina, pin.

Jensen et al., U.S. Pat. No. 6,181,960 B1, teaches a radiographic marker that is used to indicate a biopsy site and entry path. The marker has an arrow shape configuration with a shaft and a pair of limbs extending from the shaft at an angle of less than about 90.degree. The tip of the arrow indicates the biopsy site and the shaft indicates the said entry path. The marker preferable is a single piece of wire, having a diameter of less than 0.010 inches, folded to four sections, to form the limbs and shaft of the arrow. Fibers can be affixed to the shaft to cause the marker to fibrose within the tissue. An introducing device, having a body and a hub, is used to insert the marker. A cannula, dimensioned to receive the body and hub of the introducing device, has a pair of receiving channels within the interior of the body to receive the limbs of the marker.

Jones, U.S. Pat. No. 4,202,349 describes a radiopaque blood vessel marker for attachment to the side wall portions of a blood vessel during, for example, a coronary by-pass operation. The markers in the preferred embodiment are flattened, oval-shaped radiopaque discs which are attached to the outer peripheral wall portion of the blood vessel at one hundred eighty degrees (180.degree.) with respect to one another (See FIG. 3). Each radiopaque marker can be comprised of a central imbedded element of radiopaque material such as tantilum which is surrounded by a suitable plastic or like resinous material which is inert and acceptable for use within the human body. During a coronary by-pass, for example, these markers could be attached by suturing or like means to the vein graft which is itself sutured into its new position during the by-pass operation. A fluoroscopic examination by a radiologist would reveal a desirable pulsation of the graft vessel in the form of the two attached markers as the radiopaque markers will constantly move (in and out) with respect to one another. Each marker is attached to the undulating wall portion of the vessel which is constantly moved when blood flow is passing through the graft as is desirable. In the event that complications arise, and the graft becomes clotted (stopping the flow of blood therethrough), a fluoroscopic examination will reveal that the radiopaque vessel markers do not move in and out with respect to one another but rather are stationary indicating a lack of undulation and a corresponding lack of blood flow.

Elliot et al., U.S. Pat. No. 4,041,931 relates to split ring markers fabricated in whole or in part from a radiopaque material, usually metal, having the terminal ends thereof and a medial portion formed to define eyelets by means of which said marker can be sutured to the tissue at the sight of an anastomosis to provide a visual indication of its location when examined fluoroscopically.

Foerster et al., U.S. Pat. No. 5,902,310 teaches an implantable marking device which is designed to percutaneously deliver permanent markers to desired tissue locations within a patient's body, even if the desired locations are laterally disposed relative to the distal end of the delivery device, as is the case for conduit or cavity walls. This provides several advantages to the physician in diagnosis and management of tissue abnormalities, such as a means of localization of a tissue abnormality for follow-up surgical treatment, and a means of tissue abnormality site identification for purposes of ongoing diagnostic follow-up. In one preferred construction, a radiographic clip is configured in the form of a surgical staple. A disposable tissue marker applier, which comprises a flexible tube, pull wire, and squeeze handle, is employed to advance and deploy the clip to a desired tissue location. Either a flexible or a rigid introducer is also provided for providing access to the site to be marked.

Morris, U.S. Pat. No. 4,331,654 describes a drug carrier formulation consisting of magnetically-localizable, biodegradable lipid microspheres.

Granov et al., U.S. Pat. No. 5,236,410 describes a method of treatment of a tumor comprising the steps of catheterization of the arterial vessel that feeds the tumor, and transcatheter administration of a suspension of magnetically hard ferromagnetic material in an oil solution of an oil-soluble antitumor substance with simultaneous application of local magnetic field onto the area of the tumor. After 1–3 days the tumor is subjected to ultrahigh radio frequency electromagnetic field or ultrasonic waves to produce heating of the tumor tissue to the temperature of 43.0.degree.–43.5.degree. C. for a period of 5–45 minutes.

Tournier et al., U.S. Pat. No. 5,668,490, teaches suspensions of either echogenic or magnetic particles in aqueous bioadhesive carriers that effectively improve imaging by echography, respectively NMRI, of the digestive tract. Affinity of the compositions for the gastric mucosa can be adapted to the needs by appropriately selecting the carrier in function to inherent bioadhesive capacity: this technique leads to improved visualization of selected portions of the lumen.

Additional patents of interest include Dowlatshahi, U.S. Pat. No. 5,853,366, which describes a marker element which is made of radiopaque material and includes at least two leg portions of approximately equal length connected at an angle relative to each other to form a generally V-shaped resilient member that is capable of being positioned wholly within the body of a patient. A localizing device and method using the marker element for marking a tissue mass of interest are also provided. The device and method include an elongate guide member, such as a cannula, having a first end that is inserted into the body so as to be directed toward a position proximate the tissue mass of interest and an opposite second end that extends from the body. A guide path extends between the first end and the second end of the guide member. The marker element is introduced into the second end of the guide member using a Marker element dispenser and then urged along the guide path using a stylet or similar prodding member. The marker element collapses to a reduced size while being urged along the guide path, and substantially resumes its original V-shape upon discharge from the guide member so as to remain in a fixed position wholly within the body without irritating or traumatizing the surrounding tissue. A plurality of marker elements may be positioned in a similar manner to mark the tissue mass of interest.

Wichterle et al., U.S. Pat. No. 3,818,894 teaches an implant for surgical purposes which is especially useful for the operative treatment of the afflicted vocal cords, as well as to the method for its production. The implant is made from water-swellable and physiologically inert material, such as a synthetic cross-linked hydrophilic gel, and has in a dry state, when it is ready for use in an operation, the shape of a straight or bent stick provided with a sharp, pointed tip. The implant body except the tip may contain physiologically inert plasticizers.

Tucci, U.S. Pat. No. 4,545,367 teaches a detachable balloon catheter assembly which comprises a balloon and sealing valve assembly including a sealing valve being formed of a resilient material having an elongate passageway extending therethrough and being mounted in a sleeve, an inflatable balloon having a mouth portion which is bonded to the sealing valve, and a small diameter cannula having a distal end which extends through the passageway in the sealing valve. The small diameter cannula includes a connector terminal on the proximal end which is adapted to be coupled to a source of fluid pressure. The passageway in the sealing valve takes the form of an elongate slit prior to insertion of the small diameter cannula through the passageway, and upon insertion of the cannula through the passageway, the passageway takes the form of a cylindrical aperture which is in fluid-tight engagement with the outer surface of the cannula while allowing the cannula to easily slide through the passageway. When the balloon is inflated to a desired size, the cannula may be withdrawn from the passageway in the sealing valve thereby causing the passageway to revert to the slit configuration in order to provide a fluid-tight seal for the inflated balloon. In one embodiment, a piston is mounted on the small diameter cannula and an aperture extends through the side wall of the cannula so that a burst of fluid pressure may be applied to the piston causing it to be driven away from the sealing valve to drive the cannula out of engagement with the sealing valve for detachment of the cannula from the inflated sealed balloon.

Ahmed, U.S. Pat. No. 4,647,480 teaches a curing of autodeposited coatings by treatment with water or steam including a solute.

Barlow et al., U.S. Pat. No. 5,422,730 describes a method and apparatus for optical detection and imaging of regional circulatory flow in biological tissues for research purposes. An animal or plant organ is perfused with a saline suspension of colored and/or fluorescent microspheres. The organ is excised and fixed in the form of a specimen block for mounting in a microtome or other suitable apparatus. Under automatic control of a microcomputer equipped with a frame grabber, a surface layer of the block is removed, the resulting new exposed surface of the block receives a flash of illumination from a light source, and light reflected by colored microspheres or, alternatively, light emitted by fluorescent microspheres, is detected by a CCD video camera aimed at the block. Also under microcomputer control, light filters having suitable light bandpasses are interposed between the light sources and the block, and between the block and the camera. Video signals are converted by the microcomputer into position coordinates with associated optical intensities from which regional circulatory flow is computed and displayed on a monitor.

Swartz et al., teaches apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1–2 GHz range. The EPR spectra is then measured at the biological system to determine oxygen concentration. The EPR spectra is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively.

Leeb et al., U.S. Pat. No. 5,643,246, describes a system for remotely inducing a phase transition in a gel. The system includes a gel capable of volume change in response to an environmental stimulus, a seed material in contact with the gel, and generating a time-varying magnetic or a time-varying electric or electromagnetic field in the proximity of the gel to produce the environmental stimulus. In a preferred embodiment, the environmental stimulus is temperature.

Klaveness et al., U.S. Pat. No. 5,676,925, describes contrast agents comprising gas-containing or gasgenerating polymer microparticles and/or microballoons, in which the polymer is a biodegradable polymer containing units of formula —$(O)_m$—CO—O—C($R^1$ $R^2$)—O—CO—$(O)_n$— (wherein $R^1$ and $R^2$ each represent hydrogen or a carbon-attached monovalent organic group or together form a carbon-attached divalent organic group, and m and n are each independently zero or one) may be used in diagnostic applications such as ultrasound and MR imaging.

Miller et al., 0 481 685 A1, teaches a medical device for localizing a non-palpable breast lesion. The device includes a tobular introducer needle and a wire guide positioned therein for inserting into a breast to the site of the lesion.

Chapelon et al., WO 93/14712, teaches a therapudical apparatus which includes a device for treating a lesion, the locating device being connected, e.g. mechanically or electronically, to the treatment device, a device for computing the position of the lesion relative to the treatment device by means of the locating device, and a device for actuating the treatment device.

Foerster et al., WO 96/08208 A1 teaches a device used to later identify the location of a biopsy or surgery.

Foerster et al., WO 98/06346 describes an implantable marking device which is designed to percutaneously deliver permanent markers to desired tissue locations within a patient's body, even if the desired locations are laterally deposed relative to the distal end of the delivery device, as is the case for conduit or cavity walls.

The above-described references are hereby incorporated by reference in full.

The prior art teaches various implantable biomarkers. However, the prior art does not teach the improved implantable biomarker described herein. The prior art also does not teach the image guided system enabled by the implantable biomarker, and the surgical methods enabled by the invention. The present invention fulfills these needs and provides further related advantages as described in the following summary.

SUMMARY OF THE INVENTION

The present invention teaches certain benefits in construction and use which give rise to the objectives described below.

The present invention provides an implantable biomarker for finding a location inside a patient while performing minimally invasive or open surgical procedures. The implantable biomarker includes a dielectric base that includes two opposing sides from which extend a plurality of wave-guide rods. The implantable biomarker is preferably mounted upon a surgical instrument or surgical implant and used in conjunction with an image-guided system to enable a surgeon to quickly and easily find the location without requiring extensive x-rays or the use of expensive and cumbersome equipment.

A primary objective of the present invention is to provide an implantable biomarker having advantages not taught by the prior art.

Another objective is to provide an implantable biomarker that is small, inexpensive to manufacture, and easy to see with an ultrasound device.

A further objective is to provide novel methods of performing minimally invasive surgery using the implantable biomarker to quickly and accurately find specific locations within the patient.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

The above-described drawing figures illustrate the invention, an implantable biomarker 10 for finding a location inside a patient 11 or other mammalian body particularly while performing minimally invasive or open surgical procedures. The implantable biomarker 10 is used in conjunction with an image-guided system 20 to enable a surgeon to quickly and easily find the location without requiring extensive x-rays or the use of expensive and cumbersome equipment. Furthermore, in at least one embodiment, the implantable biomarker 10 enables the reporting of information about the status of a bone condition and the location to a computer 24 with a virtual image reconstruction of the body organs and real-time overlay of instruments as they course through the body as the instruments interact with bodily parts.

Implantable Biomarker

Figure 1:
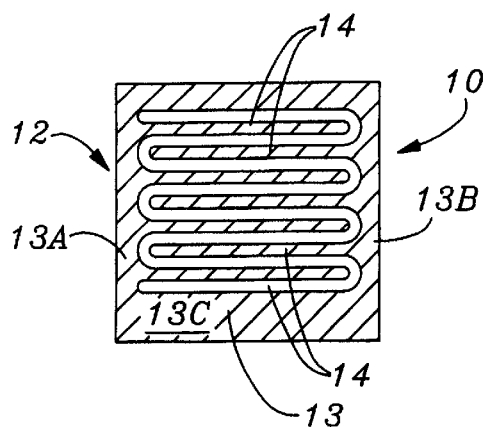
FIG. 1 is a top plan view of an implantable biomarker.

As shown in FIG. 1, the implantable biomarker 10 includes a MEMS housing 12 and a signaling means for receiving an excitation signal 17 and returning a return signal 18. The MEMS housing 12 is preferably a silicon chip that can include a biocompatible outer surface (not shown) such as paralyne or other coating well known in the art. The MEMS housing 12 is preferably approximately 1–2 mm in any dimension, or smaller, so as to minimize its interference with the surgical procedure.

In one embodiment, the signaling means includes a plurality of wave-guide features that are integral with the MEMS housing 12 and adapted to resonate when struck by an excitation signal 17 that is frequency matched or is of a given frequency and return a return signal 18. It is possible to manufacture the implantable biomarker 10 with such a small housing using MEMS manufacturing techniques that are known to those skilled in the art. Since MEMS manufacturing techniques are well known in the art, they are not described herein in greater detail.

Wave Guide Rods

In the preferred embodiment, the MEMS housing 12 includes a dielectric base 13 that includes two opposing sides 13A and 13B extending from the dielectric base 13. In this embodiment, the plurality of wave-guide features are a plurality of wave-guide rods 14 that are integral with and extend from the dielectric base 12. As shown in FIG. 1, the plurality of wave-guide rods 14 are disposed on a plane and in a parallel orientation, and each of the plurality of wave-guide rods extend from, in alternating order, one of the two opposing sides, such that each of the plurality of wave-guide rods overlaps those adjacent, between the two opposing sides.

While we state that the plurality of wave-guide rods are disposed on a plane and in a parallel orientation, this does not mean that they are limited to precisely this orientation, but only that the axis of each of the plurality of wave-guide rods is generally oriented in this fashion with respect to at least one of the others, plus or minus 8 degrees. Furthermore, since this is only the most preferred embodiment, other orientations are within the scope of the invention, and can be considered within the scope of the invention as claimed.

Means for Mounting

The dielectric base 13 also includes a means for mounting the implantable biomarker 10 on a device, typically by bonding a bottom surface 13C of the dielectric base 13 to the device or to some intermediary. In a first embodiment, shown in FIGS. 2–4, the means for mounting includes bonding the bottom surface 13C to a mounting collar 16 that is used in conjunction with a surgical instrument 26. In a second embodiment, shown in FIGS. 5 and 6, the means for mounting includes bonding the bottom surface 13C to a carrier coil 34. In a third embodiment, shown in FIG. 8, the means for mounting includes bonding the bottom surface 13C directly to a tibia nail 33. In a fourth embodiment, shown in FIG. 9C, the means for mounting includes bonding the bottom surface 13C to a screw 62 that is used to fasten a spinal appliance 60 in place. These embodiments are described in greater detail below.

In an alternative embodiment, not shown or described in greater detail, the dielectric base 13 is mounted upon a means for preventing migration of the implantable biomarker 10 when it is positioned within the mammalian body. Those skilled in the art can devise alternative embodiments, and such embodiments should be considered within the scope of the claimed invention.

First Embodiment—Tracking a Surgical Instrument

Figure 2:
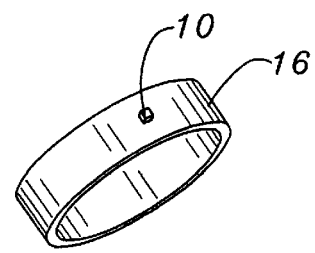
FIG. 2 is a perspective view of a collar upon which the implantable biomarker is mounted.

As shown in FIG. 2, in the first embodiment, the dielectric base 13 is mounted upon a mounting collar 16 that is adapted to be attached to a surgical instrument 28. The mounting collar 16 is an annular, low profile fixation system that is adapted to affix the implantable biomarker 10 adjacent an operative tip 28 of the surgical instrument 26.

Figure 3:
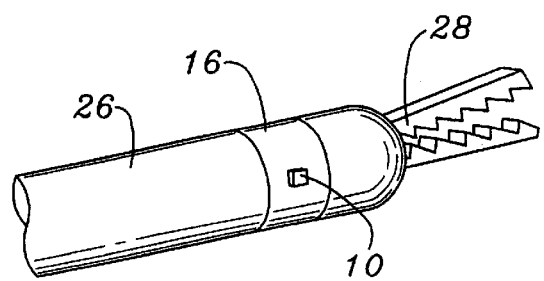
FIG. 3 is a perspective view of a surgical instrument upon which the collar is mounted.

As shown in FIG. 3, the mounting collar is adapted to affix the implantable biomarker 10 to the surgical instrument 26 adjacent the operative tip 28 without interfering with the function of the surgical instrument 26. The surgical instrument 26 used can include almost any instrument, including but not limited to endoscopes, forceps, graspers, ablation devices, suction and irrigation devices, et cetera.

Figure 4:
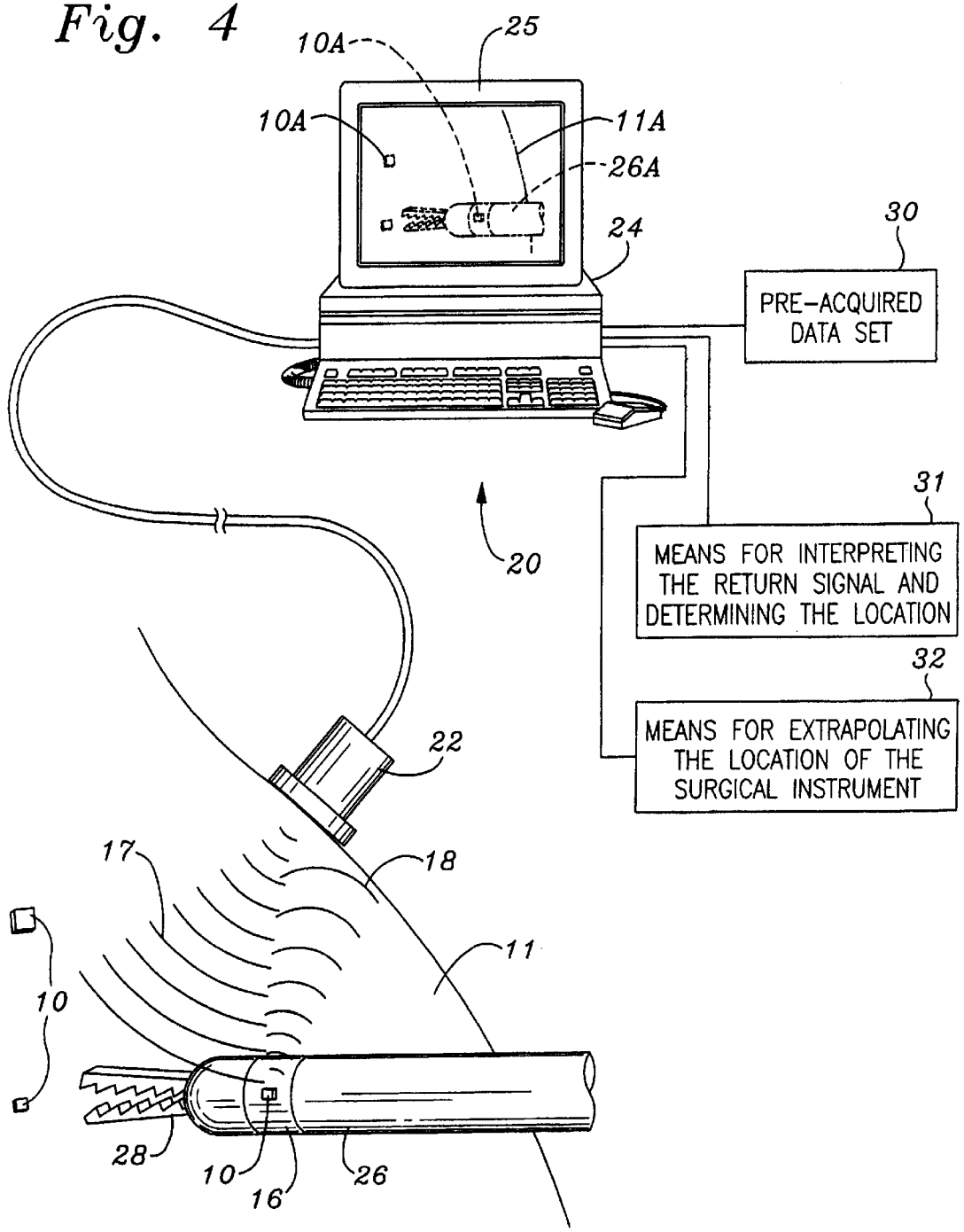
FIG. 4 is a perspective view, and partial block diagram, of an image-guided system utilizing the surgical instrument.

As shown in FIG. 4, the image-guided system 20 includes a computer 24 that is operatively attached to a transducer 22 and to a means for reporting 25 the location of the implantable marker. The transducer 22 functions to transmit the excitation signal 17 and to receive the return signal 18. In the preferred embodiment, the transducer 22 is the same as is used in an ordinary ultrasound imaging device. The means for reporting 25 is preferably a monitor or similar imaging device that functions to display the results so that the surgeon can track his or her progress, preferably in real-time. In alternative embodiments, however, the means for reporting 25 can also be provided by other visual, audio, kinesthetic, or other means for alerting the surgeon. An alternative embodiment that uses an audible tone is described in greater detail below.

In use, the computer 24 is first calibrated. A pre-acquired data set 30 is determined using any imaging devices known in the art that could include, but is not limited to, ultrasound, spiral CT, MRI, and x-ray imaging techniques. Such calibration steps for image guidance and surgical navigation are well known in the art, and are therefore not discussed in greater detail herein. The pre-acquired data set 30 is stored in the computer 24.

The computer 24 includes a means for interpreting 31 the return signal 18 and determining the location of the implantable biomarker 10. The computer also includes a means for extrapolating 35 the location of the surgical instrument 26 based upon the location of the implantable biomarker 10. These capabilities can be provided by software that can be programmed by one skilled in the art given the guidance of the present invention. Once calibrated using techniques that are known in the art, the image-guided system 20 can recognize the position of the surgical instrument 26 from the return signal 18 returned from the plurality of reeds 14 in response to the excitation signal 17 from the transducer 22.

During the operation, as shown in FIG. 4, the transducer 22 transmits the excitation signal 17 and receives the return signal 18 from the implantable biomarker 10. The computer 24 receives the data from the transducer 22 and compares the data with the data in the pre-acquired data set 30 and then the computer 24 displays the location of the surgical instrument 26 on the monitor 25. The computer 24 can generate an instrument image 26A that represents the location of the surgical instrument 26 based on the pre-acquired data set 30. The computer 24 then displays the instrument image 26A on the monitor 25 in relative position to a patient image 11A, so the surgeon is able to visualize the movement of the surgical instrument 26, in real-time, within the patient 11. The image guided system 20 is also able to display an implant image 10A relative to the patient image 11A and the instrument image 26A, either showing the location of the implantable biomarker 10 on the surgical instrument 26 or another marker that has been placed within the patient 11. Similar technology is discussed in Hunter et al., U.S. Pat. No. 6,235,038 B1, and Jonkman, U.S. Pat. No. 5,782,765, both of which are hereby incorporated by reference in full. The implantable biomarker 10 enables the function of the image-guided system 20 to enable a surgeon to accurately find the location within the patient 11 and accurately guide the surgical instrument 26 to the location within the patient 11 (in situ).

In one embodiment, the implantable biomarker 10 is calibrated to resonate and return the return signal 18 only when the excitation signal 17 is a specific frequency. In this embodiment, a plurality of the implantable biomarkers 10 can be used, each of the implantable biomarkers 10 responding to a specific frequency and emitting a unique signature moire or "waterfall effect" which is visible on the imaging monitor or computer monitor, thereby allowing the surgeon to query for specific implantable biomarkers 10 and only the target implantable biomarker 10 will respond with its unique signature. This system enables the surgeon to more easily distinguish among the plurality of implantable biomarkers 10. In this embodiment, the additional implantable biomarkers 10 can be used to mark locations within the patient 11, or to mark locations of a surgical implant 32 and to track the movement of his or her instruments in real-time, as described in greater detail below. It is also possible to include a signaling means that resonates as two or more frequencies, so that each of the implantable biomarker 10 would transmit the return signal 18 at more than one frequency.

Tracking a Surgical Implant

The implantable biomarker 10 can also be used to track a surgical implant 32. The implantable biomarker 10 can be attached directly to a variety of surgical implants 32, such as a tibia nail 33 or a spinal appliance 60, although it can be adapted to almost any surgical implant 32, and the scope of the claimed invention should be considered to include alternative structures. The implantable biomarker 10 can be attached directly to the surgical implant 32, or attached to an intermediary element such as a carrier coil 34 or a screw 62. The implantable biomarker 10 can be used to not only track the surgical implant 32, it can also be used to track a specific portion of the surgical implant 32. Examples of this construction are provided below.

Second Embodiment—Drill Guide

Figure 5:
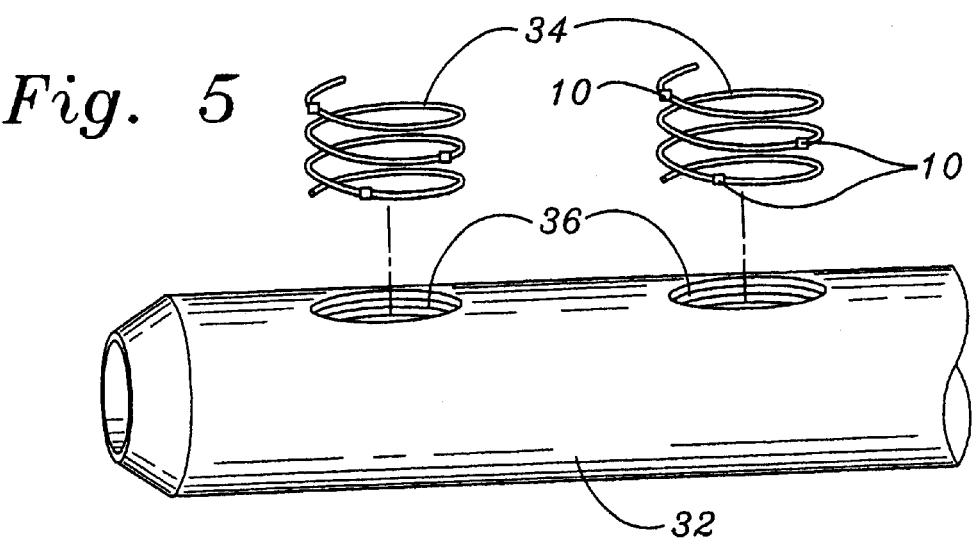
FIG. 5 is a perspective view of a tibia nail having a pair of screw-receiving apertures which each contain a carrier coil, each of the carrier coils having at least one of the implantable biomarkers mounted thereupon.
Figure 6:
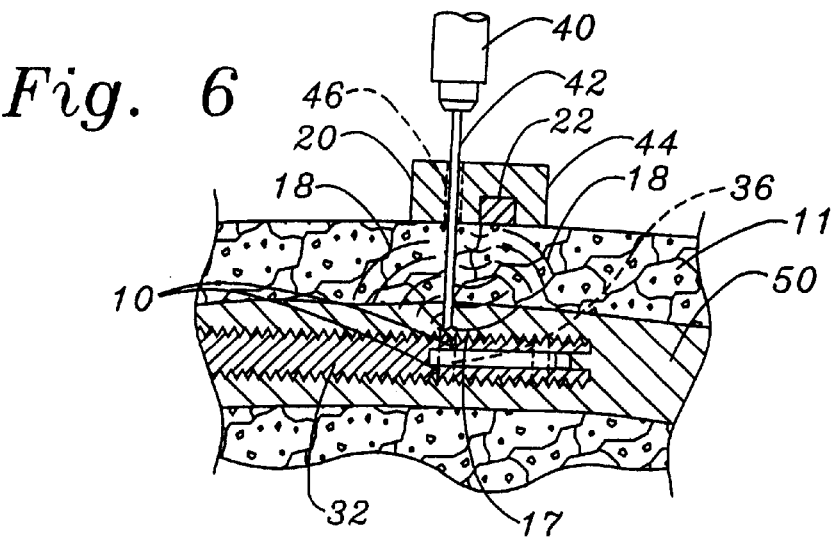
FIG. 6 is a sectional view of a surgical drill being inserted through a drill guide and guided to one of the screw-receiving apertures as directed by the implantable biomarkers.

In the second embodiment, shown in FIGS. 5 and 6, the dielectric base 13 is mounted upon a tibia nail 33 or similar orthopedic appliance so that the tibia nail 33 can be readily located during surgery; and particularly, a specific portion of the tibia nail 33 can be located. It is also possible to attach several of the implantable biomarkers 10 to the orthopedic appliance implant device so that its location and orientation can be very accurately ascertained.

As shown in FIG. 5, three of the implantable biomarkers 10 are preferably attached to each of a pair of carrier coils 34 that are adapted to be inserted into screw-receiving apertures 36 of the tibia nail 33. Of course, the surgical implant 32 could also be any of a variety of nails and screws used for similar purposes. Additionally, the implantable biomarkers 10 can be retrofitted onto pre-existing instruments, as described above.

Once the tibia nail 33 has been surgically implanted into a bone 50 of the patient 11, the implantable biomarkers 10 are used to guide the surgeon when he attempts to drill a hole through the bone 50 to one of the screw-receiving apertures 36 using a surgical drill 40. As shown in FIG. 6, the surgical drill 40 is operably positioned within a drill guide 44 so that a is drill bit 42 of the surgical drill 40 is positioned through a drill aperture 46 of the drill guide 44. The drill guide 44 is pressed against the patient 11 so that the transducer 22 that is incorporated within the drill guide 44 is able to direct the excitation signal 17 into the patient 11 and read the return signal 18 that is returned by the implantable biomarkers 10.

Figure 7:
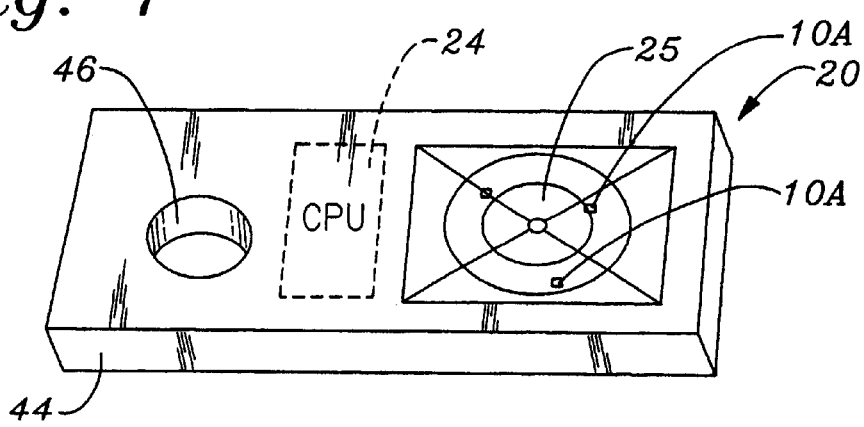
FIG. 7 is a perspective view of the drill guide.

As shown in FIG. 7, the drill guide 44 incorporates the transducer 22, the computer 24 and the means for reporting the location of one of the screw apertures 36. The means for reporting can include the monitor 25, as shown. In the preferred embodiment, the computer 24 could also emit an audible tone when the drill guide 44 is properly position. To reduce the cost of the drill guide 44, it is also possible to omit the monitor 25 and require the user to orient the drill guide 44 based on the audible tone.

The transducer 22 emits the excitation signal 17 and receives the return signal 18, and the computer 24 reads the return signal 18 returned by the implantable biomarkers 10 and generate the implant image 10A on the monitor 25 to guide the surgeon so that the surgical drill 40 is positioned to drill through one of the screw-receiving apertures 36. The drill guide 44 then emits an audible tone to indicate when the correct position and orientation has been reached. This embodiment of the image-guided system 20 is a great improvement over the prior art, which usually required the surgeon to drill multiple holes, in a trial and error fashion, to find one of the screw-receiving apertures 36.

While we specify that the output of the image-guided system 20 is the monitor 25, this is specifically anticipated to include alternative data output mechanisms such as sound or other alternative mechanism. In one alternative, the drill guide 44 could emit audible beeping tones which, when the surgical drill 40 is properly oriented, change to a continuous or otherwise modified tone.

Third Embodiment—Bone Analysis

Figure 8:
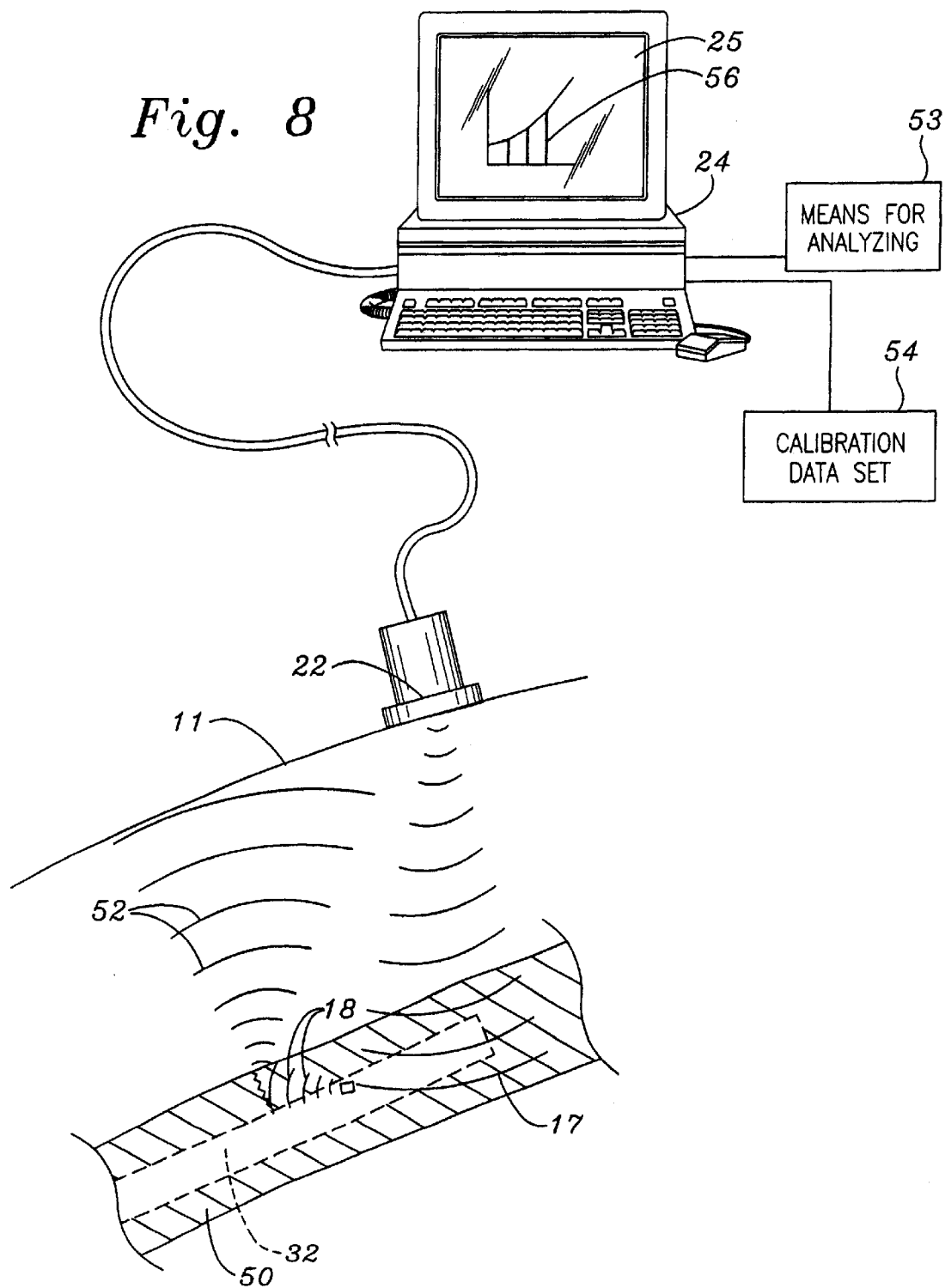
FIG. 8 is a sectional view, and partial block diagram, of the image-guided system that is adapted to be used to analyze the fusion and healing of the bone into which a surgical implant is positioned.

In another embodiment, as shown in FIG. 8, the implantable biomarker 10 is operably positioned on the tibia nail 33 to transmit the return signal 18 into the bone 50 to generate an analysis signal 52. In this embodiment, the computer 24 includes a calibration data set 54; and further includes a means for analyzing the analysis signal 52 and determining the status of fusion of the bone 50. In the preferred embodiment, the means for analyzing the analysis signal 52 is the computer 24 running software programmed and calibrated to determine the degree of fusion based on subtle changes in the analysis signal 52.

A similar system can also be adapted to sensing the healing and/or perfusion of oxygen in tissue. The analysis signal 52 is affected by subtle changes in the tissue and the oxygen content, and by comparing reading to the calibration data set 54, it is possible to monitor the healing progress of the patient 11. If healing does not progress as planned, the surgeon can take appropriate countermeasures.

Fourth Embodiment—Spinal Appliance

Figure 9C:
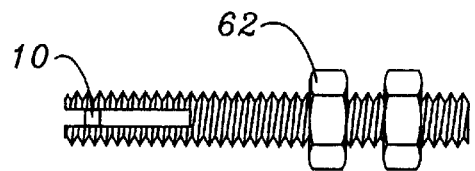
FIG. 9C is a perspective view of a screw used in the spinal appliance.
Figure 9A:
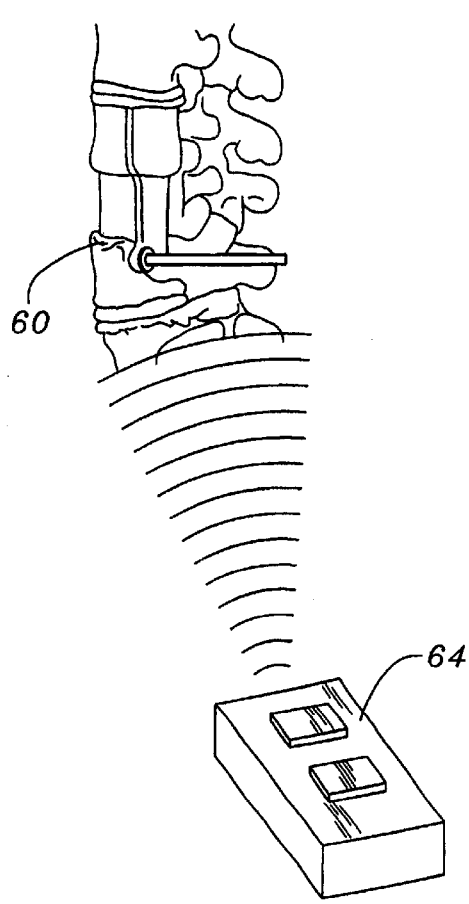
FIG. 9A is a side elevational view of a spinal appliance that incorporates the implantable biomarker.
Figure 9B:
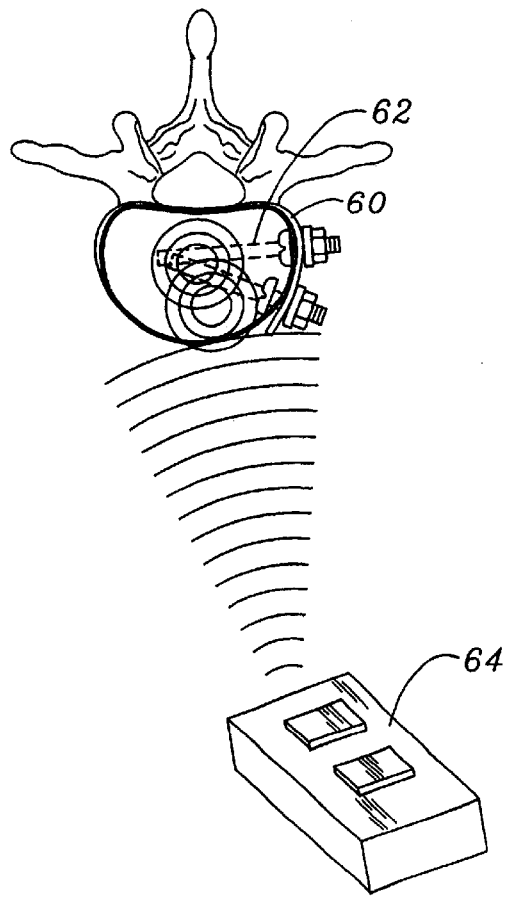
FIG. 9B is a top plan view thereof.

In another embodiment, as shown in FIGS. 9A, 9B, and 9C, the implantable biomarker 10 is incorporated into a screw 62 or other component of a spinal appliance 60. Similar to the tibia screw 33 described above, the spinal appliance 60 incorporates the implantable biomarker 10 for guiding the surgeon in drilling into the patient 11 and the bone 50 during the installation of the spinal appliance 60. Also, as described above, it is possible for the implantable biomarker 10 to transmit information about bone fusion adjacent the spinal appliance 60, and perfusion of oxygen in the surrounding tissue.

While the invention has been described with reference to at least one preferred embodiment, it is to be clearly understood by those skilled in the art that the invention is not limited thereto. Rather, the scope of the invention is to be interpreted only in conjunction with the appended claims.

All patents, patent applications, and other documents and printed matter cited or referred to in this application is hereby incorporated by reference in full.

What is claimed is:

1. An implantable biomarker for tracking a device in a mammalian body, the implantable biomarker comprising:
   a dielectric base having a means for mounting the implantable biomarker on the device; and
   a plurality of wave-guide rods, the plurality of wave-guide rods being disposed on a plane and extending from the dielectric base in a parallel orientation, the plurality of wave-guide rods being integral with the dielectric base.

2. The implantable biomarker of claim 1 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides.

3. An image guided system for tracking a device in a mammalian body, the image guided system comprising:
   an implantable biomarker having a dielectric base and a plurality of wave-guide rods, the plurality of wave-guide rods being disposed on a plane and extending from the dielectric base in a parallel orientation;
   a means for mounting the implantable biomarker on the device;
   a transducer adapted to emit an excitation signal and receive a return signal;
   a computer adapted to interpret the return signal and determine the location of the implantable biomarker, the computer being operably connected to the transducer; and
   a means for reporting the location of the implantable biomarker, the means for reporting being operably connected to the computer.

4. The image guided system of claim 3 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides.

5. The image guided system of claim 3 wherein the device to be tracked is a surgical instrument, and the means for mounting is a mounting collar adapted to be attached adjacent an operative tip of the surgical instrument.

6. The image guided system of claim 3 wherein the device to be tracked is a surgical implant, and the means for mounting is provided by directly bonding the dielectric base to the surgical implant.

7. An image guided system for tracking a surgical instrument in a mammalian body, the image guided system comprising:
   an implantable biomarker having a dielectric base and a plurality of wave-guide rods;
   a means for mounting the implantable biomarker on the surgical instrument adjacent an operative tip of the surgical instrument;
   a transducer adapted to emit an excitation signal and receive a return signal;
   a computer operably connected to the transducer,
   the computer having a means for interpreting the return signal and determining the location of the implantable biomarker,
   the computer also having a means for extrapolating the location of the surgical instrument based upon the location of the implantable biomarker; and
   a means for reporting the location of the surgical instrument, the means for reporting being operably connected to the computer.

8. The image guided system of claim 7 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides, and are disposed on a plane and in a parallel orientation.

9. The image guided system of claim 7 wherein the means for mounting is a mounting collar adapted to be attached adjacent the operative tip of the surgical instrument.

10. An image guided system comprising:
    a surgical implant;
    an implantable biomarker operably mounted on the surgical implant, the implantable biomarker having a dielectric base and a plurality of wave-guide rods;
    a transducer adapted to emit an excitation signal and receive a return signal;
    a computer operably connected to the transducer,
    the computer having a means for interpreting the return signal from the transducer and determining the location of the implantable biomarker; and
    a means for reporting the location of the surgical implant, the means for reporting being operably connected to the computer.

11. The image guided system of claim 10 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides, and are disposed on a plane and in a parallel orientation.

12. The image guided system of claim 10 wherein the surgical implant includes a screw-receiving aperture, and the implantable biomarker is operably mounted adjacent or within the screw-receiving aperture.

13. The image guided system of claim 12 wherein the implantable biomarker is mounted on a carrier coil that is shaped to fit within the screw-receiving aperture.

14. The image guided system of claim 12 further comprising a drill guide shaped to operably engage a power drill, wherein the transducer and the computer are operably positioned within the drill guide so that when the power drill within the drill guide is properly positioned to drill through the screw-receiving aperture, the transducer and computer cooperate to trigger the means for reporting.

15. A method for tracking a surgical instrument during an operation on a mammalian body, the method comprising the steps of:
    providing a surgical instrument having an implantable biomarker mounted adjacent an operative tip of the surgical instrument, the implantable biomarker having a dielectric base and a plurality of wave-guide rods;
    providing a transducer adapted to emit an excitation signal and receive a return signal, the transducer being operably connected to a computer that includes a means for interpreting the return signal from the transducer and determining the location of the implantable biomarker, the computer also having a means for extrapolating the location of the surgical instrument based upon the location of the implantable biomarker, and the computer also having a means for reporting the location of the surgical instrument; inserting the operative tip of the surgical instrument into the mammalian body; and positioning the transducer for operatively transmitting the excitation signal into the mammalian body and receiving the return signal from the implantable biomarker.

16. The method of claim 15 further comprising the step of:
    mounting the implantable biomarker on a mounting collar; and
    mounting the mounting collar adjacent the operative tip of the surgical instrument.

17. The method of claim 15 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides, and are disposed on a plane and in a parallel orientation.

18. A method for tracking a surgical implant within a mammalian body, the method comprising the steps of:
    providing a surgical implant having an implantable biomarker mounted thereon, the implantable biomarker having a dielectric base and a plurality of wave-guide rods;
    providing a transducer adapted to emit an excitation signal and receive a return signal, the transducer being operably connected to a computer that includes a means for interpreting the return signal from the transducer and determining the location of the implantable biomarker and a means for reporting the location of the surgical implant;
    inserting the surgical implant into the mammalian body; and
    positioning the transducer for operatively transmitting the excitation signal into the mammalian body and receiving the return signal from the implantable biomarker.

19. The method of claim 18 wherein the dielectric base includes two opposing sides extending from the dielectric base, and each of the plurality of wave-guide rods extend from, in alternating order, one of the two opposing sides, such that each of the plurality of wave-guide rods overlaps those adjacent, between the two opposing sides, and are disposed on a plane and in a parallel orientation.

20. The method of claim 18 wherein the surgical implant includes a screw-receiving aperture, and the implantable biomarker is operably mounted adjacent or within the screw-receiving aperture.

21. The method of claim 20 wherein the implantable biomarker is mounted on a carrier coil that is shaped to fit within the screw-receiving aperture.

22. The method of claim 20 further comprising a drill guide shaped to operably engage a power drill, wherein the transducer and the computer are operably positioned within the drill guide so that when the power drill within the drill guide is properly positioned to drill through the screw-receiving aperture, the transducer and computer cooperate to trigger the means for reporting.

* * * * *